United States Patent [19]

Goodell et al.

[11] 4,354,392

[45] Oct. 19, 1982

[54] ROTARY KILN MATERIAL SAMPLING SYSTEM

[75] Inventors: Thomas W. Goodell, Harriman; Forrest E. Clark, Lenoir City, both of Tenn.

[73] Assignee: The Direct Reduction Corporation, New York, N.Y.

[21] Appl. No.: 241,259

[22] Filed: Mar. 6, 1981

[51] Int. Cl.³ ............................................. G01N 1/20
[52] U.S. Cl. ................................................. 73/863.86
[58] Field of Search ............ 73/863.81, 863.83, 863.86

[56] References Cited

U.S. PATENT DOCUMENTS

| 3,598,377 | 8/1971 | Galliers | 73/863.81 |
| 3,613,453 | 5/1969 | Small | 73/863.86 |
| 3,675,467 | 7/1972 | Myreen | 73/863.83 |

FOREIGN PATENT DOCUMENTS 684823 12/1952 United Kingdom ............. 73/863.81

Primary Examiner—S. Clement Swisher

Attorney, Agent, or Firm—Cooper, Dunham, Clark, Griffin & Moran

[57] ABSTRACT

A system for taking samples of materials undergoing processing in a rotary kiln is disclosed in the form of a first or inner member mounted on and passing through the kiln shell and containing a chamber in direct communication with the kiln interior; a second or outer member forming an outer chamber and having one end connected to said first member; and a pivotable swing gate disposed between the inner and outer members for controlling communication between the two chambers. The outer end of the outer member has an adaptor for removably mounting a material-collecting vessel or catch can thereon. Opening of the swing gate will permit material from the kiln interior to enter the catch can without contact with the ambient environment, and subsequent closing of the swing gate permits sealing of the inner chamber in communication with the kiln interior before removal of the catch can and its contents from the end of the outer member.

8 Claims, 2 Drawing Figures

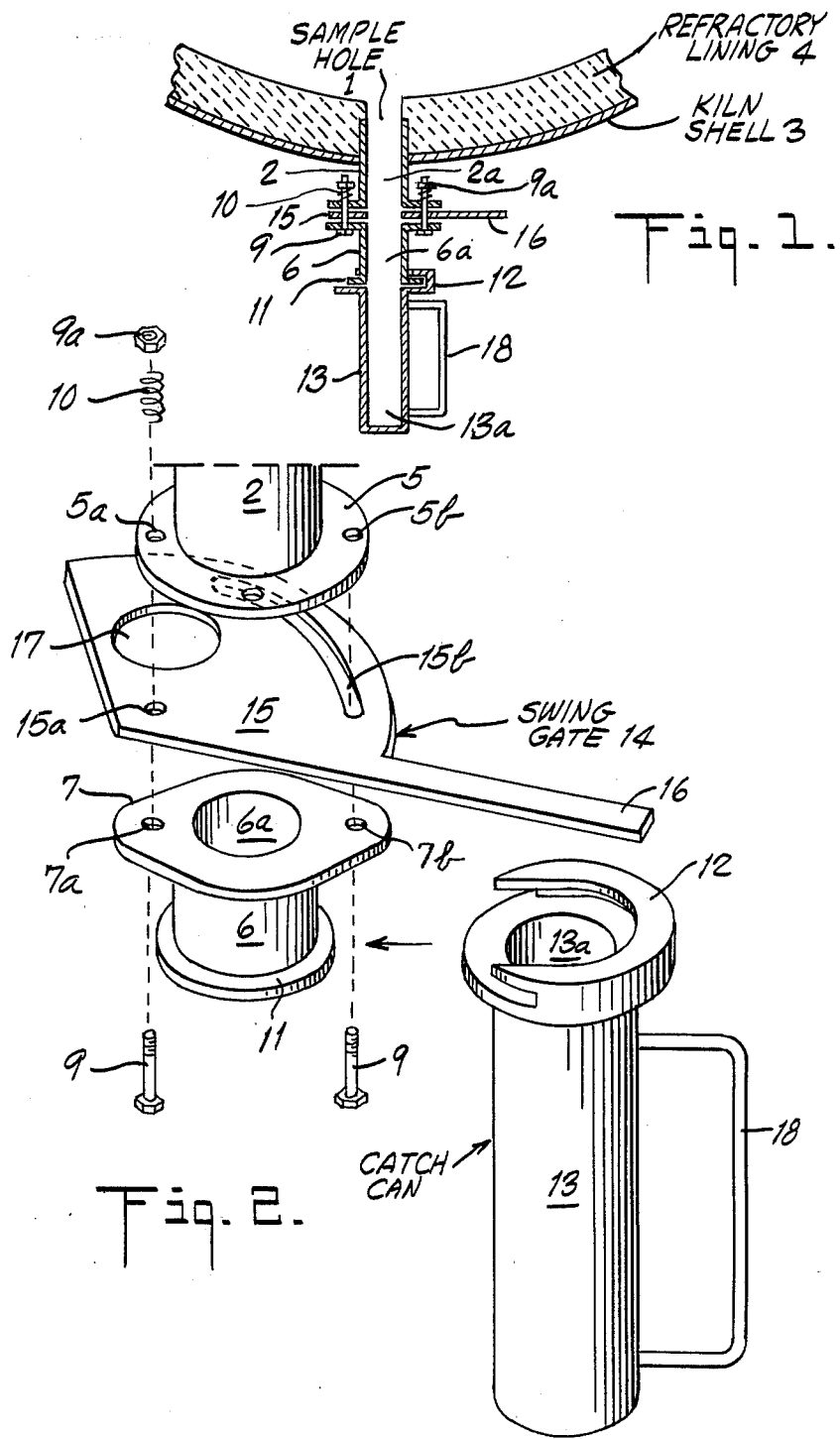

ROTARY KILN MATERIAL SAMPLING SYSTEM

BACKGROUND OF THE INVENTION

The present invention relates to an apparatus and method for removing samples of materials undergoing processing in a rotary kiln and more particularly to a system mounted on the kiln for removing materials from the kiln interior in a sealed condition.

In the course of operating a rotary kiln it is usually necessary to be able to take samples of the materials in the kiln during the process to evaluate process operation and performance. Since in many processes, such as the direct reduction of materials containing iron oxides, the kiln interior and the materials are very hot and the kiln is typically long and slender in construction, it is difficult to obtain material samples through ports or doors in the kiln ends, and since it is usually desirable to obtain samples from along the kiln length, a series of ports are conventionally formed in the kiln shell to permit withdrawal of the material samples. The closures for such ports, however, may cause problems, as they sometimes leak, spill the materials and are difficult to operate and maintain particularly in an industrial plant environment. Additionally, the material removing operation can result in contamination of the material sampled.

An example of one prior art sampling device is shown in U.S. Pat. No. 3,613,453 to Small et al and involves a sampling chamber communicating with the kiln interior and provided externally of the kiln with an inspection port, a temperature-sensing port and a material-removal port. The temperature-sensing and material-removal ports have automatically-operated pivotally mounted covers which open the sample chamber interior to the outside environment.

Another sampling device currently in use involves a sampling vessel or catch can which is attached to a gate device. The can and gate device are movable together into a position wherein an orifice in the gate device matches a sample orifice on the kiln shell permitting a sample of the material in the kiln to pass into the catch pan. The gate device is provided on one side with a hinge, having a spring loaded bolt to maintain the gate device in a sealing position, and on the other side with an operating arm which has a radius slot with a washer and spring assembly that assists the hinge bolt in maintaining the sealing. This arrangement has been found to leak material from the kiln, and occasional disconnecting of the catch can from the gate device results in spillage of material out of the kiln. Consequently, the device is unsafe and the leakage permits hot samples to interact with the outside environment causing contamination and/or chemical changes therein.

It is therefore desirable that a material sampling system for recovering samples of materials being processed in a rotary kiln be provided that will maintain sealing of the kiln and sampling system while operating easily and safely to remove samples, and additionally that will seal hot samples for a cooling period to avoid contamination or chemical change. The present invention provides such a sampling system of rugged construction and simple design with a minimum of moving parts and which maintains appropriate sealing of the kiln and sample.

SUMMARY OF THE INVENTION

The present invention embodies a rotary kiln material sampling system involving a single moving part in the form of a swing gate which controls communication between an inner chamber communicating with the kiln interior and an outer chamber communicating with a catch can which is attached thereto. More particularly, the inner chamber is contained in a cylindrical member mounted on and passing through the kiln shell and having a circular pipe flange on its outer end, and the outer chamber is contained in a second cylindrical member having a mating oval shaped pipe flange connectable to the circular or ring flange on the first cylindrical member. The second cylindrical member also has a ring flange on its opposite end to which the catch can is slidably attached. The swing gate is disposed between the two oval flanges and has a pivot hole and a 90° arcuate slot therein through which two spring-loaded bolts respectively pass that hold the flange and gate assembly together in a sealing relationship. The swing gate is in the form of an acute sector with an outwardly extending operator arm for pivoting it through approximately a 90° arc about the pivot belt. The sector has a sample passing aperture at one end of its arc and is solid at the other end to block communication between the two chambers.

In operation, the swing gate is rotated from the closed position, wherein communication between the two chambers is blocked, through about a 90° arc in which position the sample passing aperture registers with the two chambers so that materials in the kiln are permitted to pass through the two chambers into the catch can. With the swing gate in the open position, as the kiln rotates the sampling system will pass under the bed of materials permitting the materials to drop by gravity into the catch can. The can may then be permitted to rotate through at least one kiln revolution with the swing gate open thereby allowing the catch can after filling with material to empty its contents back into the kiln as it rotates above the bed, thus preheating the catch can and allowing any leftover material therein to drop out. After the catch can is again filled with kiln materials on passing beneath the bed, the swing gate may be closed by rotating it through a 90° arc in the reverse direction from opening, and the catch can may be allowed to remain on the sampling system for several further revolutions of the kiln until the sample or specimen of material is cooled. The can may then be slidably removed from the ring flange and the cooled materials taken for testing and analysis.

It will be seen that the present sampling system is quite easy to operate, requiring only the movement of the swing gate through a 90° arc. Also, no movement of the catch can or other parts is required during the sampling operation, and the swing gate acts to isolate the kiln interior and the sampled materials from the ambient atmosphere during sampling, thus avoiding the chance of contamination or chemical change during the cooling of the sample.

BRIEF DESCRIPTION OF THE DRAWINGS

FIG. 1 is a diagrammatic view in section illustrating the sampling system of the present invention mounted on a rotary kiln shell.

FIG. 2 is an exploded perspective view illustrating in detail the structural parts of the present sampling system.

DETAILED DESCRIPTION OF THE INVENTION

A system in accordance with the present invention mounted on the wall of a rotary kiln is shown in FIG. 1. The system may be mounted in a sample hole 1 of the type formed in one or more locations along the length of a rotary kiln in which materials are being processed, and particularly, for example, in a rotary kiln in which materials containing iron oxides are being directly reduced using solid carbonaceous materials as the source of fuel and reductant to produce sponge iron or directly reduced iron (DRI). A cylindrical member 2 of heat-resistant material such as steel is fitted in the sample hole 1 and extends in sealing relationship through the kiln shell 3 into the refractory lining 4. The inner open end of the cylindrical member 2 communicated directly with the kiln interior so that samples of the materials being processed in the kiln will drop into the chamber 2a in the member 2 when the sample hole 1 passes under the materials bed during kiln rotation.

The opposite end of cylindrical member 2 disposed outside of the kiln shell 3 may be formed with a standard circular pipe flange 5 which is adapted to connect member 2 to a like cylindrical member 6, such as by two holes, 5a and 5b of four equally spaced holes therein for accommodating the passage of bolts, or like fastening means, as seen in greater detail in FIG. 2. The second cylindrical member 6 may be provided with an oval-shaped flange 7 having matching holes 7a and 7b toward each end to permit it to be attached to the first cylindrical member 2 by a suitable fastening arrangement such as spring-loaded bolts 9. The bolts 9 are respectively passed through the mating holes 5a, 7a, and 5b, 7b and draw the adjacent faces of flanges 5 and 7 together under the action of springs 10 which are held on the remote side of either flange by means of mounting nuts 9a.

On the opposite end of cylindrical member 6 from oval flange 7 there is formed a circular or ring flange 11 which accommodates a mating closure assembly 12 formed on the upper end of a sample receptacle or catch can 13. It will be seen that when the closure assembly 12 is slid into full mating relationship with the ring flange 11 the interior 13a of the catch can 13 will be in sealed communication with the chamber 6a in cylindrical member 6.

Disposed in sliding relationship between the adjacent faces of flanges 5 and 7 on the first and second cylindrical members 2 and 6 is a swing gate 14 in the form of a plate member having an acute sector portion 15 with an outwardly extending operator arm 16. The sector portion 15 is formed near its apex with a bolt hole 15a which cooperates with the flange holes 5a and 7a in passing one of the bolts 9. An arcuate slot 15b extending through an arc of about 90° is formed in the sector adjacent its rounded edge and cooperates with flange holes 5b and 7b in passing the other bolt 9. The slot 15b permits the swing gate 14 to be pivoted about bolt hole 15a slidingly between the adjacent faces of flanges 5 and 7 which are caused to bear resiliently against the upper and lower surfaces of the sector 15 by the spring-loading of the bolts 9. The bolt 9 passing through slot 15b limits the travel of swing gate 14 to an arc equal to that of the slot. The sector 15 is also formed toward one straight edge with a sample passing aperture 17 which, when the sector is pivoted to one of its limits of travel, cooperates with the chambers 2a and 6a in the first and second cylindrical members 2 and 6 to permit unimpeded communication between the chambers 2a and 6a. The portion of the sector 15 adjacent to the other straight edge is solid so as to totally block communication between the two chambers 2a, 6a when the sector 15 is pivoted to its opposite limit of travel from that in which the sample passing aperture 17 cooperates with the chambers. With the solid portion of the sector 15 in the position cutting off communication between the chambers 2a, 6a the interior of the kiln will be sealed from the ambient atmosphere through the action of the spring-loaded bolts 9 pressing the adjacent faces of flanges 5 and 7 tightly against the opposite faces of the swing gate 14. On the other hand, when the swing gate 14 is pivoted by means of operator arm 16 to the position wherein communication is opened between chambers 2a and 6a, it will be seen that if the catch can 13 is properly mounted on ring flange 11, then samples of material may drop from the kiln through sample hole 1 along the passage formed by communicating chambers 2a and 6a into the interior 13a of the catch can 13 without contact with the ambient atmosphere.

During normal operation of the kiln, swing gate 14 will be maintained in the closed position and a catch can need not be mounted on the outer end of the cylindrical member 6. When it is desired to obtain a sample of the materials being processed in the kiln, the catch can 13 is attached by means of its mounting assembly 12 to the ring flange 11 on cylindrical member 6 such that the can interior 13a communicates in a sealed manner with the outer end of chamber 6a, the inner end of which chamber is sealed by the solid portion of swing gate 14. The swing gate 14 is then rotated from the closed position, wherein communication between chambers 6a and chamber 2a is blocked, through an arc of about 90° to the open position in which the sample passing aperture 17 registers with the two chambers so that materials in the kiln are permitted to pass through the two chambers into the catch can 13. As the kiln rotates with the swing gate 14 in the open position, the sampling system will pass under the bed of hot materials within the kiln causing some of the materials to drop by gravity through the sample hole 1 into the catch can 13. The system may then be permitted to rotate through at least one kiln revolution with the swing gate open, thereby allowing the catch can, after receiving the materials, to empty its contents back into the kiln as it rotates above the bed. The filling of the catch can 13 with hot materials preheats the can and the subsequent emptying allows any leftover material from a previous sampling to drop out with the hot materials, thus readying the can for a fresh sample. During continuing rotation the catch can 13 is again filled with kiln materials on passing beneath the bed, after which the swing gate 14 may be closed by rotating it with operator arm 16 back through an arc of about 90° in the reverse direction from opening. The catch can may then be allowed to remain on the sampling system for several further revolutions of the kiln until the materials of the sample or specimen are cooled. Thereafter the can may be slidably removed from the ring flange and the cooled materials taken therefrom for testing and analysis.

As the swing gate 14 will be in the closed position, the removal of the can 13 from the remainder of the system will not result in the ambient atmosphere coming in contact with any of the kiln materials. Further, the closing of the gate before the removal of the catch can permits the sample or specimen to be isolated from the kiln interior and the ambient atmosphere while cooling thus reducing the chances of sample contamination. It will be seen that the only operating motions required for sampling are the pivoting of the swing gate 14 and the advancing of the catch can 13 onto the ring flange 11, while holding the can by the handle 18, without any rotary motion of the can. The simple construction of the system accordingly provides for an easy and uncomplicated sampling operation during which desirable sealing is continuously maintained.

We claim:

1. Apparatus for removing samples of materials being processed in a rotary kiln comprising:

first means passing through the kiln shell for defining a first chamber communicating with the kiln interior;

second means connected at one end to said first means exteriorly of the kiln shell for defining a second chamber communicating with said first chamber;

gate means disposed between said first and second means and movable between an open position and a closed position for respectively opening and closing off the communication between said first and second chambers; and receptacle means removably connected to the other end of said means for receiving material samples passing through said first and second chambers from the kiln interior when said gate means is in said open position.

2. Apparatus as in claim 1 wherein said first means is a cylindrical member having a flange on its exterior end and said second means comprises a cylindrical member having flange means on one end for connecting it to said flange on said first means and said gate means comprises a member sealing slidable through an arc of about 90° between said flange and said flange means.

3. Apparatus as in claim 2, further comprising spring loaded bolt means for connecting said flange and said flange means together.

4. Apparatus as in claim 2 wherein said flange comprises a ring flange having four equally spaced bolt holes therein, and said flange means comprises an oval shaped flange having a bolt hole toward each end in matching relationship with opposing pairs of said four equally spaced bolt holes.

5. Apparatus as in claim 4, wherein said gate means comprises a flat sector shaped means having a bolt hole near its apex in mating relationship with one of said four equally spaced bolt holes, and one of said bolt holes in said oval shaped flange, and further comprising spring loaded bolt means passing through said three mating holes for connecting said first means, said gate means, and said second means together.

6. Apparatus as in claim 1 wherein second means has a ring flange on said other end and said receptacle means comprises means on its receiving end for sealingly sliding onto said ring flange.

7. Apparatus as in claim 1 wherein said gate means comprises a flat sector-shaped member having an aperture toward one of the straight sides thereof for opening communication between said first and second chambers.

8. Apparatus as in claims 5 or 7, wherein said sector shaped member included an arcuate slot means therein for passing a connecting bolt therethrough, and further comprising operator arm means for pivoting said sector shape member between the limits of said slot means.

* * * * *